US009863931B2

(12) United States Patent
Newman et al.

(10) Patent No.: US 9,863,931 B2
(45) Date of Patent: Jan. 9, 2018

(54) ON-BOARD CONTROL DETECTION

(75) Inventors: Peter Michael Newman, Victoria (AU); Alastair M. Hodges, Victoria (AU)

(73) Assignee: Universal Biosensors Pty Ltd, Rowville, Victoria (AU)

( * ) Notice: Subject to any disclaimer, the term of this patent is extended or adjusted under 35 U.S.C. 154(b) by 0 days.

(21) Appl. No.: 13/264,926

(22) PCT Filed: Apr. 16, 2010

(86) PCT No.: PCT/IB2010/000972
§ 371 (c)(1),
(2), (4) Date: Oct. 17, 2011

(87) PCT Pub. No.: WO2010/119341
PCT Pub. Date: Oct. 21, 2010

(65) Prior Publication Data
US 2012/0040369 A1 Feb. 16, 2012

Related U.S. Application Data
(60) Provisional application No. 61/170,440, filed on Apr. 17, 2009.

(51) Int. Cl.
G01N 33/50 (2006.01)
G01N 33/49 (2006.01)
C12Q 1/00 (2006.01)
G01N 33/543 (2006.01)
(52) U.S. Cl.
CPC ......... *G01N 33/4905* (2013.01); *C12Q 1/006* (2013.01); *G01N 33/5438* (2013.01); *Y10T 436/144444* (2015.01)

(58) Field of Classification Search
None
See application file for complete search history.

(56) References Cited

U.S. PATENT DOCUMENTS

| | | | |
|---|---|---|---|
| 4,426,451 A | 1/1984 | Columbus | |
| 6,066,448 A | 5/2000 | Wohlstadter et al. | |
| 6,872,299 B2 | 3/2005 | Kermani et al. | |
| 2002/0092612 A1 | 7/2002 | Davies | |
| 2003/0180814 A1 | 9/2003 | Hodges | |
| 2005/0067301 A1 | 3/2005 | Morita et al. | |
| 2005/0123441 A1 | 6/2005 | Unkrig | |

(Continued)

FOREIGN PATENT DOCUMENTS

| | | |
|---|---|---|
| CN | 1589400 A | 3/2005 |
| EP | 1380837 | 1/2004 |

(Continued)

OTHER PUBLICATIONS

PCT International Preliminary Report on Patentability in corresponding International application No. PCT/IB2010/000972, dated Sep. 24, 2010, 7 pages.

(Continued)

*Primary Examiner* — Erik B Crawford
(74) *Attorney, Agent, or Firm* — Hahn Loeser & Parks LLP

(57) ABSTRACT

Embodiments disclosed herein relate to a sensor comprising an on-board control system and a testing system. The on-board system can determine viability of the control system or the testing system. Also disclosed are methods of using such a sensor.

22 Claims, 4 Drawing Sheets

(56) References Cited

U.S. PATENT DOCUMENTS

| | | |
|---|---|---|
| 2006/0134713 A1 | 6/2006 | Rylatt |
| 2006/0266644 A1 | 11/2006 | Pugh |
| 2007/0193882 A1* | 8/2007 | Dai .................... G01N 27/3272 204/403.02 |
| 2007/0205103 A1 | 9/2007 | Hodges |
| 2010/0006452 A1 | 1/2010 | Hodges |

FOREIGN PATENT DOCUMENTS

| | | |
|---|---|---|
| JP | 2003-524162 | 8/2003 |
| JP | 2003-262604 | 9/2003 |
| JP | 2003-529062 | 9/2003 |
| JP | 2004-053363 | 2/2004 |
| JP | 2005-156544 | 6/2005 |
| JP | 2008-076407 | 4/2008 |
| WO | WO 2000/006761 | 2/2000 |
| WO | WO 2001/057238 | 8/2001 |
| WO | WO 2002/008763 | 1/2002 |
| WO | WO 2004/061444 | 7/2004 |
| WO | WO 2007/096730 | 8/2007 |
| WO | WO 2008/010058 | 1/2008 |
| WO | WO 2008/050145 | 5/2008 |
| WO | WO 2009/053834 | 4/2009 |
| WO | WO 2010/004436 | 2/2010 |
| WO | WO 2010/119341 | 10/2010 |

OTHER PUBLICATIONS

Office Action, mailed in related Chinese Patent Application No. 201080016852.X, dated Jul. 10, 2013.
Japan Patent Office, "Official Action (English translation only)," mailed in corresponding Japan Patent Application No. 2012-505251, dated Dec. 16, 2014, 2 pgs.
Australian IP Office, "Patent Examination Report," mailed in corresponding Australia Patent Application No. 2010238253, dated May 28, 2014, 4 pgs.
Intellectual Property Office of New Zealand, "Examination Report," mailed in corresponding New Zealand Patent Application No. 596284, dated Oct. 2, 2012, 1 pg.
Israel Patent Office, "Office Action (English translation only)," mailed in corresponding Israel Patent Application No. 215791, dated Aug. 31, 2014, 3pgs.
Japan Patent Office, Official Action (English translation only) mailed in corresponding Japan Patent Application No. 2012-505251, dated Jan. 14, 2014, 2 pgs.
Mexican Institute of Industrial Property, Office Action mailed in corresponding Mexican Patent Application No. MX/a/2011/010823, dated Apr. 8, 2014, 3 pgs.
Mexican Institute of Industrial Property, Office Action mailed in corresponding Mexican Patent Application No. MX/a/2011/010823, dated Sep. 3, 2014, 2 pgs.
State Intellectual Property Office of the People's Republic of China, "Official Action (English translation only)," mailed in corresponding China Patent Application No. 201080016852.X, dated Jul. 10, 2013, 1 pg.
Taiwan Intellectual Property Office, "Official Action (English translation only)," mailed in corresponding Taiwan Patent Application No. 099112002, dated Dec. 8, 2014, 5 pgs.
State Intellectual Property Office of the People's Republic of China, "Official Action (English translation only)," mailed in corresponding China Patent Application No. 201080016852.X, dated Aug. 18, 2015.
European Patent Office, "Extended European Search Report," mailed in corresponding European Patent Convention Application No. 10764162.3, dated Oct. 29, 2014.
Israel Patent Office, "Office Action (English translation only)," mailed in corresponding Israel Patent Application No. 215791, dated Dec. 7, 2015.
Intellectual Property Office of New Zealand, "Examination Report," mailed in corresponding New Zealand Patent Application No. 596284, dated Mar. 26, 2014.
Intellectual Property Office of New Zealand, "Examination Report," mailed in corresponding New Zealand Patent Application No. 596284, dated Oct. 15, 2015.
Taiwan Intellectual Property Office, "Official Action (English translation only)," mailed in corresponding Taiwan Patent Application No. 099112002, dated Aug. 25, 2015.

* cited by examiner

ON-BOARD CONTROL DETECTION

CROSS-REFERENCE TO RELATED APPLICATIONS

The present application is a U.S. National Stage entry under 35 U.S.C. §371 of International Application No. PCT/IB2010/000972, filed on Apr. 16, 2010, designating the United States of America and published in English on Oct. 21, 2010, which in turn claims priority to U.S. Provisional Application No. 61/170,440, filed on Apr. 17, 2009, each of which is hereby incorporated by reference in its entirety.

BACKGROUND

There has been a proliferation of on-site analytical and diagnostic measurement kits. Non-limiting examples include those used in environmental science and health care, such as household lead test kits, on-site water contamination test kits, home blood glucose test kits, home pregnancy test kits, and home blood coagulation test kits. Merely by way of example, point-of-care tests based on a meter that measures an electrochemical reaction in a disposable test strip are becoming increasingly common. Many of these meters are designed for use by health care professionals but also for people less familiar with their use such as consumers who purchase them for use at home. As these meters can play a major role in monitoring important health conditions (e.g., blood glucose levels or coagulation times) to evaluate, monitor, and/or determine proper therapeutic treatments, there is a need to ensure that test results are accurate. One such way to ensure the accuracy of these results can include using a control system to determine test strip viability.

SUMMARY

Embodiments of the application include a sensor for assessing a sample. The sample can include a fluid sample or a solid sample. The sensor can comprise an on-board control system and a testing system. The control system can comprise at least one reagent for determining viability of at least one of the control system and the testing system via a control reaction. The at least one reagent can be free of N-oxide or a nitroso compound.

In some embodiments, the control reaction generates a control signal. The control signal can comprise at least one selected from an electrical signal, an optical signal, a color, and a chemical signal. Thus, in some embodiments, the control system can comprise an electrochemical control system. In certain embodiments, the control reaction can be assessed without an external voltage. For example, the control reaction can be activated upon contacting the at least one reagent with a composition, wherein the contacting generates a control signal. In some embodiments, the composition can comprise the sample. In some embodiments, the composition can comprise an external stress. The external stress can comprise at least one selected from temperature, pH, humidity, oxygen, light, shelf time, and a chemical contamination, or the like.

In some embodiments, the control system can comprise at least two electrodes, wherein the at least one reagent can be coated on at least one of the electrodes. The at least two electrodes can be coplanar. The at least two electrodes can be opposing to each other. In some embodiments, the control reaction can generate an electromotive force. For example, the electromotive force can be generated by dissolution of the at least one reagent into the sample. In some embodiments, the at least one reagent can comprise ferricyanide. The area loading of ferricyanide coated on at least one of the electrodes can be from about $10 \times 10^{-6}$ to about $200 \times 10^{-6}$ moles per square meter. In some embodiments, the at least one reagent can comprise a neutralizing agent, wherein the neutralizing agent can neutralize the control signal via a neutralizing effect. The neutralizing effect can comprise at least one selected from a chemical reaction and a physical effect. The physical effect can comprise at least one selected from precipitation and diffusion.

The testing system can comprise at least one selected from an immunological testing system, a blood glucose testing system, and a blood coagulation testing system. The control system and the testing system can be located in one chamber. The control system can be located in a first chamber, and at least part of the testing system can be located in a second chamber. The first chamber and the second chamber can be in parallel fluid connection. The first chamber and the second chamber can be in serial fluid connection via a sample passageway.

Embodiments of the application include a method of measuring a sample using a sensor comprising: applying the sample to the sensor, wherein the sensor comprises an on-board control system and a testing system, wherein the control system comprises at least one reagent for determining viability of at least one of the control system and the testing system via a control reaction, wherein the at least one reagent is free of N-oxide or a nitroso compound, wherein the control reaction generates a control signal, comparing the control signal with a standard signal to determine viability of the at least one of the control system and the testing system; and measuring the sample in the testing system. The control system can comprise an electrochemical control system.

In some embodiments, the control reaction can be assessed without an external voltage. For example, the control reaction can be activated upon contacting the at least one reagent with the sample, wherein the contacting can generate a control signal. The control signal can comprise at least one selected from an electrical signal, an optical signal, a color, and a chemical signal. In some embodiments, the control system can comprise at least two electrodes, wherein the at least one reagent is coated on at least one of the electrodes. The at least two electrodes can be coplanar. The at least two electrodes can be opposing to each other.

In some embodiments, the control reaction can generate an electromotive force. The electromotive force can be generated by dissolution of the at least one reagent into the sample. In some embodiments, the at least one reagent can comprise ferricyanide. The area loading of ferricyanide coated on at least one of the electrodes can be from about $10 \times 10^{-6}$ to about $200 \times 10^{-6}$ moles per square meter. In some embodiments, the at least one reagent can comprise a neutralizing agent, wherein the neutralizing agent can neutralize the signal via a neutralizing effect. The neutralizing effect can comprise at least one selected from a chemical reaction and a physical effect. The physical effect can comprise at least one selected from precipitation and diffusion.

In some embodiments, the testing system can comprise at least one selected from an immunological testing system, a blood glucose testing system, a blood coagulation testing system, and the like. In some embodiments, the control system and the testing system can be located in one chamber. In other embodiments, the control system can be located in a first chamber, and at least part of the testing system can be located in a second chamber. The first chamber and the second chamber can be in parallel fluid connection. The first chamber and the second chamber can be in serial fluid connection via a sample passageway. In some embodiments, sample can be transferred from the first chamber to the second chamber. The transferring can comprise a capillary action.

Some embodiments relate to methods that include measuring at least one reaction selected from an immunological reaction and an electrochemical reaction. The methods can comprise measuring at least one test signal selected from an electrical signal and an optical signal. In some embodiments, the sample can comprise blood, wherein the measuring can comprise measuring blood coagulation rate or blood glucose concentration.

DETAILED DESCRIPTION

Figure 1:
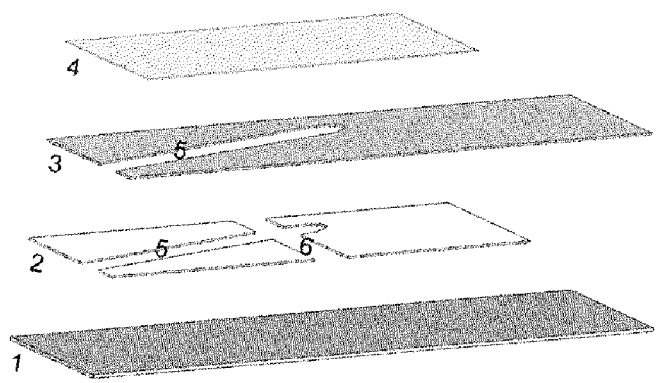
FIG. 1 shows an exploded view of an exemplary electrochemical biosensor with a single chamber.

Various embodiments of an on-board control system are described herein. Some embodiments are described in connection with a biosensor and/or a test strip merely for illustration purposes, and is not intended to limit the scope of the application. It is understood that the on-board control system is applicable to other types of systems, such as, for example, sensors or on-site test kits, or any system or device whose viability can be verified in order to perform its intended use properly. Merely for the purpose of simplicity, an on-board control system is referred to as a control system herein.

As used herein, an on-board control system refers to one integrated into a biosensor and/or a test strip that can verify the viability of the same. Examples of on-board control systems can be found in the area of point-of-care coagulation devices on the market including, for example, Coaguchek XS and INRatio. An introduction to the advantages of an on-board control system can be found in, for example, U.S. Patent Application Publication No. 2005/0123441 by Unkrig et al. (hereinafter referred to as "Unkrig"), which is hereby incorporated herein by reference in its entirety.

As used herein, a biosensor can include a meter for measurement.

The more isolated the control reaction is from the test reaction, the more complicated an electrochemical biosensor typically becomes. For example, in order of increasing complexity:

A biosensor or test strip with a single reaction chamber that includes both a control reaction and a test reaction is comparatively easy to manufacture.

A biosensor or test strip with control and test chambers that are separate but electrically connected is more complicated as it requires deposition of multiple reagents in different areas.

A biosensor or test strip with control and test chambers that are not only separate but also electrically isolated can be quite challenging to manufacture economically at scale. It usually requires deposition or ablating electrode material in a pattern.

However, the difficulty in finding suitable control reaction chemistry is in the reverse order to that above. For example, a biosensor or test strip with separate, and electrically isolated, control and test chambers may not encounter any problems with one reaction (e.g., a control reaction) interfering with the other reaction (e.g., a test reaction). In comparison, a biosensor or test strip with separate, but electrically connected, control and test chambers can suffer from electrical interference between the chambers as electrons from one reaction are indistinguishable from electrons from the other reaction, but the control reaction and test reaction may not interfere with each other chemically. On the other hand, a biosensor or test strip with a single reaction chamber typically requires components or reagents that will not interfere with each other chemically or cause interfering electrical signals.

The Unkrig reference discloses an on-board control reaction utilizing N-oxide or nitroso compounds that become reduced upon exposure to conditions that may damage strip performance, wherein the change in on-board control can be detected optically or electrochemically. In practice, electrochemical detection in electrochemical devices is favored because this detection method does not require the additional components, such as optical detection equipment or colorimetric dyes, that optical detection methods may need.

For example, the electrochemical detection method disclosed in Unkrig can involve applying a voltage of about −700 mV, relative to Ag/AgCl, for about 3 seconds across the working electrode, and then applying a voltage of about −100 mV for about 1.5 seconds. The first potential can be a preparing phase and the second potential the measuring phase for the on-board control. Then assessment of the test (e.g., coagulation) reaction can follow.

However, in some cases, evaluating a control reaction by applying a voltage across an electrochemical sensor, as taught in the art, can have a deleterious effect on a subsequent test reaction in a testing system. As one example, the applied voltage can generate undesirable concentration gradients of reactants and/or undesirable products between the electrodes. As another example, the currents from the control reaction can interfere with the test reaction.

The on-board control system disclosed in embodiments described herein can overcome such problems. For example, in some embodiments, the on-board control system does not require an external voltage for the control reaction to occur. Alternatively, in some embodiments, the control system can employ a control reaction in which the generated control signal can dissipate or be neutralized before the test reaction is evaluated.

As used herein, a "control reaction" refers to a reaction that occurs to generate a control signal which can be evaluated to determine, for example, but not limited to, viability of at least one of the control system and the testing system; and a "test reaction" refers to a reaction that occurs to generate a test signal which can be evaluated to determine, qualitatively or quantitatively, at least one composition of interest of a sample. A control reaction can include a chemical reaction that generates a control reaction product, wherein the control reaction product can comprise a composition or property that is different from at least one of the reactant ingredients involved in the control reaction including, for example, the sample or the reagent of the control system. A control reaction can include a physical process that can be driven by, for example, a concentration gradient of at least one of the reactant ingredients involved in the control reaction including, for example, the sample or the reagent of the control system. A control reaction can include a combination of a chemical reaction and a physical process.

A test reaction can include a chemical reaction, a physical process, or a combination thereof.

As used herein, "viability" refers to the suitability of a control system or a testing system to perform an intended measurement or test. Viability can include at least one property that can impact measurement of a control system and/or a testing system. Viability can depend on, for example, accuracy of measurement, a predictable correlation between a measured result and a derived result, or the like, or any combination thereof. Viability of a control system or a testing system can be compromised by, for example, a shelf time which is longer than suggested, an improper (e.g., too hot, too humid) storage condition, exposure to an acid or a base, (extended) exposure to light or air (oxygen), exposure to a chemical contamination (e.g., a household chemical which can react with at least one reagent or a reactant ingredient of the control system or the testing system), or the like, or any combination thereof.

Embodiments of the application include a biosensor for assessing a sample, wherein the biosensor can comprise an on-board control system and a testing system. The sample can be fluid or solid. The control system can comprise at least one reagent for determining viability of at least one of the control system and the testing system via a control reaction. The reagent can be free of N-oxide or a nitroso compound. The control reaction can generate a control signal.

In an electrochemical biosensor the on-board control system can include an electrochemical control reaction. The control system can be designed such that the electrical signal of the control reaction and that of the test reaction do not interfere with each other. This can avoid the need to electrically isolate the control system from the testing system.

In some embodiments, the control system can be designed to generate its own voltage (also referred to as electromotive force or EMF) or current without the need to externally apply a voltage to the electrodes of the test strip. It is well known to those skilled in the art that a voltage or current can be generated by immersing two suitable electrodes in suitable electrolyte. The electrodes, and/or the electrolyte surrounding them, can be different in order to generate a voltage difference between the electrodes. Usually different electrolytes do not mix, but they can be connected by a salt bridge. Mixing of the electrolytes can result in a loss of EMF. Normally this can be undesirable. However, some embodiments of the present application include a control system that takes advantage of this property to generate a short-lived EMF in the control reaction.

The control system can include at least one reagent. The reagent can bring about a control reaction which can generate a control signal. The reagent can be chosen based on the desired mechanism of the control reaction and/or that of the test reaction. In some embodiments, the reagent does not interfere with the test reaction. The control signal can be used to determine viability of the control system or the testing system of the biosensor.

In some embodiments, the control reaction can be assessed without an external voltage. This can reduce the chances that the testing system is compromised by an external voltage before a test reaction is performed.

The control reaction can be activated upon contacting the reagent with a composition to generate a control signal. In some embodiments, the composition can include the sample to be measured using the biosensor. The sample can include, for example, blood, urine, saliva, or any other bodily fluid, or any combination thereof. In addition, the composition can include samples of interest other than a bodily fluid. Merely by way of example, for a water contamination test kit, the composition can include the water to be assessed.

In other embodiments, the composition can include, for example, an enzyme, a catalyst, a buffer or a solvent that can facilitate the control reaction. The composition can be inert to the control reaction and/or the test reaction. The composition can accelerate the control reaction and/or the test reaction. The composition can react to the reagent and/or the sample and/or any part of the testing system for the control reaction and/or the test reaction to occur. The composition can be stored in the biosensor (e.g., in a compartment of the biosensor) and can be released by a user (e.g., by crushing the compartment or by generating an opening of the compartment using a piercing means such as a needle, by removing a tape or by other means). The composition can dissolve into the sample. The composition can be added by a user before, concurrently with, or after application of the sample.

In further embodiments, the composition can include an external stress that can impair viability of the control system or the testing system. Merely by way of example, the external stress can include at least one selected from temperature, pH, humidity, oxygen, light, shelf time, a chemical contamination, and the like. Such external stress can cause, for example, oxidation of a reagent or a reactant ingredient involved in the control reaction and/or the test reaction, fouling of an electrode involved in measurement of the control reaction and/or the test reaction, or the like, or any combination thereof.

The control reaction can generate a control signal. The control signal can comprise at least one selected from an electrical signal, an optical signal, a color, and a chemical signal, or the like, or any combination thereof. Viability of the control system or the testing system can be evaluated based on the control signal at a single time point or over a time period. Viability can be evaluated before the test reaction is activated and/or evaluated.

In some embodiments, the control reaction can generate an electrical signal, e.g., a voltage and/or a current. The control signal can be different depending on whether the control system or the testing system is viable. Merely by way of example, the control signal can be different in terms of the peak value (including magnitude and/or direction), the area under the peak(s), the number of peaks, the mean value over a time period, the change of the value with time over a time period, or the like, or any combination thereof. Differences in the electrical signal can be due to the differential electromotive forces generated in the control reaction depending on viability of the control system and/or the testing system. The electromotive forces can be generated by, for example, a concentration gradient of an electroactive compound between two electrodes.

The electrical signal can be measured at a single time point or over a time period, both of which can be between a starting point and an endpoint. The starting point can be when the control reaction is activated as described above. The endpoint can be when the control reaction stops, or when the control signal dissipates and becomes too small to be measured. As an example, the control reaction can stop due to exhaustion of at least one of the reactant ingredients involved in the control reaction. Such reactant ingredient can include, for example, the sample and the reagent of the control system. The exhaustion can be due to, for example, consumption, precipitation, or the like, or a combination thereof, of at least one of such reactant ingredients. As another example, the control reaction can stop because the electromotive forces dissipate when the concentration gradient of an electroactive compound (e.g., in the sample and/or in the reagent of the control system) disappears and the electroactive compound reaches equilibrium by, for example, diffusion. The control signal can dissipate due to a neutralization effect comprising a neutralizing agent. Merely by way of example, when the sample is added, the control reaction can produce a voltage difference or some other electrochemical signal but can be then quickly neutralized by the neutralizing agent. The neutralizing effect can be by a chemical reaction (e.g., iodine and ascorbate can neutralize each other) or a physical effect such as, for example, precipitation (e.g., $Co^{2+}$, $Mn^{2+}$ or $Zn^{2+}$ ions can precipitate ferricyanide). Precipitation of an electroactive compound can render it incapable of interacting with an electrode.

In some embodiments, the reagent of the control system can be used as at least one reactant ingredient involved in the test reaction. The control reaction and the test reaction can be activated or proceed under different conditions. Merely by way of example, the control reaction can be activated upon application of the sample to the control system to generate a control signal, wherein the control signal is measured and/or recorded and dissipates before the test reaction is activated; while the test reaction can be activated upon application of an external voltage at a specific time point to generate a test signal which is assessed and/or recorded. The control signal and the test signal can be differentiated based on the time point when the test reaction is activated. As another example, the test reaction can involve an additional reactant ingredient(s) which can be applied at a time point different from application of the sample. The control signal and the test signal can be differentiated based on the time point when the test reaction is activated by application of the additional reactant ingredient(s). The additional reactant ingredient(s) can be applied in a controlled fashion by, for example, coating the additional ingredient(s) in a different chamber or an otherwise different portion of the biosensor. Alternatively, the additional reactant ingredient(s) can be such that its dissolving rate into the sample can depend on the presence and/or quantity of the control signal or a product of the control reaction. Accordingly, the test reaction can be activated depending on the status and/or progress of the control reaction.

In other embodiments, the reagent of the control system can be different from the reactant ingredient(s) involved in the test reaction. The change in the reagent of the control system can correlate with viability of the test reaction or a reactant ingredient involved in the test reaction. In some aspects, such correlation can result from, for example, parallel property shift under substantially the same condition. As used herein, "parallel property shift" refers to that the change in at least one property of the reagent of the control system is substantially similar to or correlated with that of at least one reactant ingredient of the testing system under substantially the same condition (e.g., storage condition). Merely by way of example, in one embodiment, the reagent of the control system and at least one reactant ingredient of the testing system both can be sensitive to humidity. The control signal generated by the control reaction involving the reagent can indicate when the reactant ingredient has degraded or otherwise changed due to excess humidity to the extent that viability of the control system and/or the testing system is compromised and the biosensor becomes unsuitable for the intended use. In other aspects, such correlation can be due to, for example, a change in cross reactivity between the reagent of the control system and at least one reactant ingredient of the testing system.

Merely by way of example, under proper storage conditions, the reagent of the control system is inert with respect to the reactant ingredient of the testing system; while when exposed to excess humidity, the reagent of the control system can react with the reactant ingredient of the testing system such that viability of the control system and/or the testing system is compromised and the biosensor becomes unsuitable for the intended use.

The reagent(s) of the control system can be chosen based on considerations including, desired mechanism of the control reaction and/or test reaction, the sample to be assessed using the biosensor, reactant ingredients involved in the control reaction and/or test reaction, proper storage condition, cost, or the like, or a combination thereof. The control system can include one or more reagents. In some embodiments, the control system can include reagents with different stabilities to produce an on-board control reaction that has a biphasic control signal or sensitivities to different conditions. For example, a control system can include at least two of the following reagents, wherein a first reagent can be sensitive to high temperature, and a second reagent can be sensitive to humidity, a third reagent can be sensitive to a change in pH value of the ambient, and a fourth reagent can be sensitive to light.

Merely by way of example, the control system can include at least one reagent selected from, iodine, ascorbate, ferricyanide, ferrocyanide, 4-amino-2-chlorophenol, or the like, or any combination thereof.

The reagent of the control system can be coated (e.g., dried) or otherwise supported on a portion of the control system, for example, at least one electrode or an internal surface of the control system. The area loading of the reagent can be chosen depending on the property of the reagent, the mechanism of the control reaction and/or the test reaction, or the like, or a combination thereof. Merely by way of example, the area loading of a reagent to generate a voltage difference as the control reaction (e.g., ferricyanide on the electrode or an internal surface of the control system) can be from about $1 \times 10^{-6}$ to about $1000 \times 10^{-6}$ moles per square meter, or from about $2 \times 10^{-6}$ to about $800 \times 10^{-6}$ moles per square meter, or from about $5 \times 10^{-6}$ to about $500 \times 10^{-6}$ moles per square meter, or from about $10 \times 10^{-6}$ to about $200 \times 10^{-6}$ moles per square meter. The area loading of the reagent can be at least about $1 \times 10^{-6}$ moles per square meter, or at least about $2 \times 10^{-6}$ moles per square meter, or at least about $5 \times 10^{-6}$ moles per square meter, or at least about $10 \times 10^{-6}$ moles per square meter, or at least about $25 \times 10^{-6}$ moles per square meter, or at least about $50 \times 10^{-6}$ moles per square meter, or at least about $75 \times 10^{-6}$ moles per square meter, or at least about $100 \times 10^{-6}$ moles per square meter, or at least about $150 \times 10^{-6}$ moles per square meter, or at least about $200 \times 10^{-6}$ moles per square meter, or at least about $250 \times 10^{-6}$ moles per square meter, or at least about $300 \times 10^{-6}$ moles per square meter, or at least about $400 \times 10^{-6}$ moles per square meter, or at least about $500 \times 10^{-6}$ moles per square meter, or at least about $1000 \times 10^{-6}$ moles per square meter. The area loading of the reagent can be lower than about $1000 \times 10^{-6}$ moles per square meter, or lower than about $800 \times 10^{-6}$ moles per square meter, or lower than about $500 \times 10^{-6}$ moles per square meter, or lower than about $400 \times 10^{-6}$ moles per square meter, or lower than about $300 \times 10^{-6}$ moles per square meter, or lower than about $250 \times 10^{-6}$ moles per square meter, or lower than about $200 \times 10^{-6}$ moles per square meter, or lower than about $150 \times 10^{-6}$ moles per square meter, or lower than about $100 \times 10^{-6}$ moles per square meter, or lower than about $75 \times 10^{-6}$ moles per square meter, or lower than about $50\times10^{-6}$ moles per square meter, or lower than about $30\times10^{-6}$ moles per square meter, or lower than about $25\times10^{-6}$ moles per square meter, or lower than about $20\times10^{-6}$ moles per square meter, or lower than about $15\times10^{-6}$ moles per square meter, or lower than about $10\times10^{-6}$ moles per square meter. As used herein, about indicates ±20% variation of the value it describes.

In some embodiments, the control system can include an electrochemical control reaction measured using two electrodes. Merely by way of example, the control reaction can be generated by a concentration gradient of ferricyanide between the electrodes. For example, in one embodiment, a first electrode can be coated with a reagent that contains a low area loading of ferricyanide (e.g., from about $10\times10^{-6}$ to about $200\times10^{-6}$ moles per square meter); and a second electrode can be substantially free of ferricyanide (e.g., by coating a reagent completely without or substantially without ferricyanide). When a sample is added between the first electrode and the second electrode, the reagent coated on the first electrode (and the reagent coated on the second electrode if available and dissolvable) can dissolve into the sample. Initially, the solution close to the first electrode contains a higher concentration of ferricyanide than the solution close to the second electrode. In some embodiments, this can create a voltage difference between the first electrode and the second electrode. The voltage difference can be measured directly. Alternatively, the electrodes can be connected by a low impedance electrical connection and the resultant current can be measured through an external circuit. The testing system can also include an electrochemical test reaction comprising an amperometric or voltametric assessment. In order not to interfere with the assessment of the test reaction, the electrical signal (current or voltage) can dissipate before the assessment by at least two methods: 1) current flowing through an external circuit can effectively counterbalance or flatten the electrochemical voltage difference and/or 2) diffusion of ferricyanide from one electrode to the other can decrease the ferricyanide concentration gradient and thus the voltage difference.

The electrical signal can be measured at a single time point between a starting point and an endpoint of the control reaction as described above. The measurement can be made at about 0.01 seconds, or about 0.05 seconds, or about 0.1 seconds, or about 0.2 seconds, or about 0.5 seconds, or about 0.8 seconds, or about 1 second, or about 1.5 seconds, or about 2 seconds, or about 2.5 seconds, or about 3 seconds, or about 3.5 seconds, or about 4 seconds, or about 4.5 seconds, or about 5 seconds, or about 6 seconds, or about 7 seconds, or about 8 seconds, or about 9 seconds, or about 10 seconds, or about 15 seconds, or about 20 seconds, or about 25 seconds, or about 30 seconds, or longer than about 30 seconds after the control reaction is activated. The measurement can be made no later than about 0.01 seconds, or about 0.05 seconds, or about 0.1 seconds, or about 0.2 seconds, or about 0.5 seconds, or about 0.8 seconds, or about 1 second, or about 1.5 seconds, or about 2 seconds, or about 2.5 seconds, or about 3 seconds, or about 3.5 seconds, or about 4 seconds, or about 4.5 seconds, or about 5 seconds, or about 6 seconds, or about 7 seconds, or about 8 seconds, or about 9 seconds, or about 10 seconds, or about 15 seconds, or about 20 seconds, or about 25 seconds, or about 30 seconds after the control reaction is activated.

The electrical signal can be measured over a time period between a starting point and an endpoint of the control reaction as described above. The measurement can start at about 0.01 seconds, or about 0.05 seconds, or about 0.1 seconds, or about 0.2 seconds, or about 0.5 seconds, or about 0.8 seconds, or about 1 second, or about 1.5 seconds, or about 2 seconds, or about 2.5 seconds, or about 3 seconds, or about 3.5 seconds, or about 4 seconds, or about 4.5 seconds, or about 5 seconds, or about 6 seconds, or about 7 seconds, or about 8 seconds, or about 9 seconds, or about 10 seconds, or about 15 seconds, or about 20 seconds, or about 25 seconds, or about 30 seconds, or Longer than about 30 seconds after the control reaction is activated. The measurement can start no later than about 0.01 seconds, or about 0.05 seconds, or about 0.1 seconds, or about 0.2 seconds, or about 0.5 seconds, or about 0.8 seconds, or about 1 second, or about 1.5 seconds, or about 2 seconds, or about 2.5 seconds, or about 3 seconds, or about 3.5 seconds, or about 4 seconds, or about 4.5 seconds, or about 5 seconds, or about 6 seconds, or about 7 seconds, or about 8 seconds, or about 9 seconds, or about 10 seconds, or about 15 seconds, or about 20 seconds, or about 25 seconds, or about 30 seconds after the control reaction is activated. The measurement can last about 0.1 seconds, or about 0.5 seconds, or about 1 second, or about 1.5 seconds, or about 2. seconds, or about 2.5 seconds, or about 3 seconds, or about 3.5 seconds, or about 4 seconds, or about 4.5 seconds, or about 5 seconds, or about 6 seconds, or about 7 seconds, or about 8 seconds, or about 9 seconds, or about 10 seconds, or about 15 seconds, or about 20 seconds, or about 25 seconds, or about 30 seconds, or longer than about 30 seconds. The measurement can last shorter than about 0.1 seconds, or shorter than about 0.5 seconds, or shorter than about 1 second, or shorter than about 1.5 seconds, or shorter than about 2. seconds, or shorter than about 2.5 seconds, or shorter than about 3 seconds, or shorter than about 3.5 seconds, or shorter than about 4 seconds, or shorter than about 4.5 seconds, or shorter than about 5 seconds, or shorter than about 6 seconds, or shorter than about 7 seconds, or shorter than about 8 seconds, or shorter than about 9 seconds, or shorter than about 10 seconds, or shorter than about 15 seconds, or shorter than about 20 seconds, or shorter than about 25 seconds, or shorter than about 30 seconds, or shorter than about 40 seconds, or shorter than about 50 seconds, or shorter than about 1 minute, or shorter than about 1.5 minutes, or shorter than about 2 minutes, or shorter than about 3 minutes, or shorter than about 4 minutes, or shorter than about 5 minutes. The measurement can last longer than about 0.1 seconds, or longer than about 0.5 seconds, or longer than about 1 second, or longer than about 1.5 seconds, or longer than about 2. seconds, or longer than about 2.5 seconds, or longer than about 3 seconds, or longer than about 3.5 seconds, or longer than about 4 seconds, or longer than about 4.5 seconds, or longer than about 5 seconds, or longer than about 6 seconds, or longer than about 7 seconds, or longer than about 8 seconds, or longer than about 9 seconds, or longer than about 10 seconds, or longer than about 15 seconds, or longer than about 20 seconds, or longer than about 25 seconds, or longer than about 30 seconds.

The time period in which the electrical signal is measured and the control reaction lasts can be chosen such that the control reaction does not substantially interfere with assessment of the test reaction.

Viability of the control system or the testing system can be determined based on the electrical signal measured at a single time point between a starting point and an endpoint of the control reaction as described above. Viability can be determined by, for example, comparing the electrical signal with a pre-determined standard value including magnitude and/or direction. In some embodiments, viability is confirmed if the electrical signal is about the same as the standard value. In other embodiments, viability is confirmed if the electrical signal is higher or lower than the standard value.

Viability of the control system or the testing system can be determined based on the electrical signal measured over a time period between a starting point and an endpoint of the control reaction as described above. For example, viability can be determined using the electrical signal over about the entire time period, or over a portion of time period. In some embodiments, viability can be determined using the electrical signal directly. Merely by way of example, viability can be confirmed if the time-dependent electrical signal matches a pre-determined standard profile. In other embodiments, the electrical signal can be processed or transformed before it is used to evaluate viability. Merely by way of example, the electrical signal can be processed or transformed to obtain the peak value(s) including magnitude and/or direction, the area under the peak(s), the number of peaks, the time when a peak appears, how long a peak sustains, how quickly a peak dissipates, the mean value over at least a portion of the time period, or the like, or a combination thereof. Viability can be determined by, for example, comparing the electrical signal with a pre-determined standard value including, for example, magnitude, direction, or the like, or a combination thereof.

Viability of the control system or the testing system can be determined by, for example, comparing the electrical signal, with or without processing or transformation, to a standard value. The comparison can be performed using a device, e.g., a computer or a data processer. The device can be incorporated into the biosensor or meter. The result, whether the biosensor is viable or not, can be reported through an audio device, (e.g., a speaker), a visual device (e.g., a screen), a printer, or the like, or a combination thereof. In some embodiments, the comparison can be performed manually by, e.g. a user. Merely by way of example, in some embodiments, a user can compare the electrical signal, with or without processing or transformation, printed to a screen or a paper to a standard value to determine viability of the control system or the testing system. Alternatively, in some embodiments, the meter does not directly report the control system result but rather determines whether or not the control system signal indicates a viable or non-viable test system. Thus, in some embodiments, if the determination is that the test system is viable then the meter presents a test result to the user, and if the test system is determined to be non-viable an appropriate error message is displayed to the user.

In some embodiments, there is a correlation between the control reaction and the test reaction. Merely by way of example, shift in the properties of a reactant ingredient involved in the test reaction can be detected quantitatively in the control reaction, and deviation of the ultimate result due to the shift can be corrected using a correction coefficient, wherein the correction coefficient can be a function of the electrical signal generated in the control reaction. The control reaction can serve as a calibration, in addition to the viability test, of the test reaction, and can provide the correction coefficient for the test reaction based on the electrical signal to ensure accuracy of the ultimate result. As used herein, the ultimate result refers to that generated by assessing the sample using the biosensor according to its intended use. The ultimate result can indicate at least one property of a composition of interest in the sample. The property can include, e.g., presence of absence, concentration, or the like, or a combination thereof.

In some embodiments, the control reaction can generate a chemical signal depending on whether the control system or the testing system is viable. Merely by way of example, in an exemplary embodiment, the testing system of a biosensor can be sensitive to humidity. When the biosensor is exposed to excess humidity, the control system of the biosensor can generate a chemical ingredient upon activation of the control reaction. Such a chemical ingredient can include, for example, an antagonist of the composition of interest in the sample, an inhibitor of an enzyme involved in the test reaction, an analogue of the antigen of interest in the sample which can bind to the corresponding antibody of the testing system, or the like, or a combination thereof.

In some embodiments, the composition of interest in the sample and the testing system of the biosensor can be intact after the control reaction regardless of the mechanism and/or reagents involved in the control reaction when viability of the control system or the testing system is confirmed or compromised. That is, in some embodiments, the control reaction does not impair the intended use of the biosensor when viability of the control system or the testing system is confirmed or compromised. In other embodiments, the composition of interest in the sample and the testing system of the biosensor can be intact after the control reaction regardless of the mechanism and/or reagents involved in the control reaction when viability of the control system or the testing system is confirmed. In some embodiments, the composition of interest in the sample or the testing system of the biosensor can be impaired after the control reaction when viability of the control system or the testing system is compromised.

The control reaction can generate a control signal of the same type as that of the test signal generated by the test reaction. Merely by way of example, both the control reaction and the test reaction can generate an electrical signal, or an optical signal. The control signal and the test signal can be measured and/or recorded using the same device or the same type of devices, and can be differentiated by the different time points when the control reaction or the test reaction is activated. In some embodiments, the control signal can dissipate before the test signal is measured and/or recorded, such that it does not interfere with the test signal. This can simplify the biosensor and/or its use because one type of measurement device is needed.

In some embodiments, the control reaction can generate a control signal of a different type than that of the test signal generated by the test reaction. Merely by way of example, the control reaction can generate an optical signal, while the test reaction can generate an electrical signal. The control signal and the test signal can be measured and/or recorded using different devices.

It is understood that the on-board control system described above is applicable to a wide range of systems or devices, such as, for example, biosensors, sensors or on-site test kits, whose viability can be verified in order to perform their intended use. Merely by way of example, suitable applications include, but are not limited to, a biosensor for assessing blood coagulation, glucose, cholesterol, immunoassays, or the like, or any combination thereof. Descriptions of such biosensors can be found in, for example, PCT Publication No. WO2002/008763, entitled "IMMUNOSENSOR", filed Jul. 13, 2001; U.S. Application Publication No. 20030180814, entitled "DIRECT IMMUNOSENSOR ASSAY", filed Mar. 21, 2002; U.S. Application Publication No. 20060134713, entitled "BIOSENSOR APPARATUS AND METHODS OF USE", filed Nov. 21, 2005; U.S. Patent Application Publication No. 20100006452, entitled "BIOSENSOR APPARATUS AND METHODS OF USE", filed Sep. 18, 2009; PCT Publication No. WO2008/010058, entitled "ELECTROCHEMICAL DETECTION OF MAGNETIC PARTICLE MOBILITY", filed Jul. 13, 2007; PCT Publication No. WO2009/053834, entitled "APPARATUS AND METHOD FOR ELECTROCHEMICAL DETECTION", filed Oct. 25, 2008; PCT Publication No. WO 2010/004436, entitled "ENHANCED IMMUNOASSAY SENSOR", filed Jul. 19, 2009, each of which is incorporated herein by reference in its entirety. As described above, the application is described in connection with a biosensor merely for illustration purposes, is not intended to limit the scope of the application.

In some embodiments, a biosensor for assessing a sample can comprise an on-board control system and a testing system. The sample can be fluid or solid. The control system can comprise at least one reagent for determining viability of at least one of the control system and the testing system via a control reaction. The reagent can be free of N-oxide or a nitroso compound. The control reaction can generate a control signal. The testing system can perform a test reaction using the sample to assess a composition of interest in the sample. The biosensor can include a single chamber or multiple chambers.

Thus, in some embodiments, the biosensor can include a single chamber. The control system and the testing system can be located in the same chamber. In some embodiments, the control signal and the test signal are of the same type (e.g., an electrical signal, an optical signal). The control signal and the test signal can be differentiated based on, for example, the different time points when the control reaction and the test reaction are activated or measured, respectively. In some embodiments, the control reaction and the test reaction can be separated apart by at least about 0.1 seconds, or at least about 0.2 seconds, or at least about 0.3 seconds, or at least about 0.4 seconds, or at least about 0.5 seconds, or at least about 0.6 seconds, or at least about 0.7 seconds, or at least about 0.8 seconds, or at least about 0.9 seconds, or at least about 1 second, or at least about 1.2 seconds, or at least about 1.5 seconds, or at least about 1.8 seconds, or at least about 2 seconds, or longer than 2 seconds. In some embodiments, the control reaction and the test reaction can be separated apart by less than about 60 seconds, or less than about 50 seconds, or less than about 40 seconds, or less than about 30 seconds, or less than about 20 seconds, or less than about 15 seconds, or less than about 10 seconds, or less than about 8 seconds, or less than about 5 seconds, or less than about 3 seconds, or less than about 2 seconds, or less than about 1.5 seconds, or less than about 1.2 seconds, or less than about 1 second, or less than about 0.8 seconds, or less than about 0.5 seconds. In other embodiments, the control signal and the test signal can be of different types (e.g., one is an electrical signal and the other is an optical signal). For example, the control signal and the test signal can be differentiated based on the type of the signals. In further embodiments, the control signal can prevent the test reaction from occurring if the control system or the testing system is not viable. See the description above.

In some embodiments, the biosensor can include two chambers. The test reaction can include one or more phases (e.g., the immunological reaction and electrochemical detection in an electrochemical immunoassay). In some embodiments, the control reaction and the test reaction can be located in separate chambers. In some embodiments, the control reaction and part of the test reaction (e.g., the immunological reaction) can be located in the same chamber, while other part of the test reaction can be located in the other chamber.

In some embodiments, the two chambers can be in parallel fluid connection. For example, the control reaction and the test reaction can be located in separate chambers. The control reaction and the test reaction can occur substantially independent from each other.

In some embodiments, the two chambers can be in serial fluid connection. For example, the control reaction and part of the test reaction (e.g., the immunological reaction) can be located in a first chamber, while another part of the test reaction (e.g., the electrochemical detection) can be located in a second chamber. The sample can flow from the first chamber to the second chamber through a sample passageway. The sample passageway can be an open passageway. The sample can flow from the first chamber to the second chamber via a capillary action. In some embodiments, the second chamber can include a vent which can be opened by a user. The second chamber can generate a greater capillary attraction force than the first chamber. The greater capillary force can be due to, for example, smaller capillary dimension, hydrophilic surfactant, or the like, or a combination thereof. Alternatively, the capillary force of the second chamber can be equal to or less than the capillary force of the first chamber but greater than the capillary force of another chamber of the strip in fluid connection with the first and second chamber of the strip. For example, the second chamber and the first chamber can have greater capillary force than a third sample introduction chamber. In some embodiments, the sample can be stopped at the open sample passageway between the first and the second chamber by the air trapped in the second chamber, and can flow to the second chamber upon opening the vent by, e.g., piercing, or the like. Such a design is described in, for example, PCT Publication No. WO2002/008763, entitled "IMMUNOSENSOR", filed Jul. 13, 2001; U.S. Application Publication No. 20030180814, entitled "DIRECT IMMUNOSENSOR ASSAY", filed Mar. 21, 2002; U.S. Application Publication No. 20060134713, entitled "BIOSENSOR APPARATUS AND METHODS OF USE", filed Nov. 21, 2005; U.S. Patent Application Publication No. 20100006452, entitled "BIOSENSOR APPARATUS AND METHODS OF USE", filed Sep. 18, 2009; each of which is incorporated herein by reference in its entirety. The sample passageway can include a junction stop (e.g., a meniscus control). The sample can flow from the first chamber to the second chamber by an external pressure sufficient to push the sample cross the junction stop. Description about such a junction stop can be found in, for example, U.S. Pat. No. 4,426,451, entitled "MULTI-ZONED REACTION VESSEL HAVING PRESSURE-ACTUATABLE CONTROL MEANS BETWEEN ZONES", issued Jan. 17, 1984, which is incorporated herein by reference in its entirety. The sample passageway can include a barrier layer comprising at least one porosity which can generate a retention force for the sample. The sample can flow from the first chamber to the second chamber by disturbing the retention force. For example, the retention force can be disturbed by contacting a surface in the second chamber which is not coplanar with the barrier layer with the sample in the barrier layer. Such a design can be found in, for example, PCT Publication No. WO 2007/096730, entitled "FLUID TRANSFER MECHANISM", filed Feb. 15, 2007, which is incorporated herein by reference in its entirety. The control signal and the test signal can be differentiated by controlling when to advance the sample from the first chamber to the second chamber.

In some embodiments, the biosensor can include more than two chambers. Merely by way of example, the biosensor can include a fill chamber, in addition to the two chambers in parallel fluid connection or in serial fluid connection described above. As another example, the biosensor can comprise three chambers, wherein the control system can be located in a first chamber, and different parts of the testing system (e.g., the immunological reaction and the electrochemical detection) can be located in a second chamber and a third chamber, respectively. In some embodiments, the first chamber can be in parallel fluid connection with the second chamber, and the second chamber can be in serial fluid connection with the third chamber. In other embodiments, all three chambers can be in serial fluid connection. There can be a sample passageway as describe above between any two of the chambers.

The chamber can include at least one internal surface. As used herein, an internal surface can comprise an internal wall which can define the cross-sectional shape and/or volume of the interior of the chamber. The internal wall(s) can comprise, but are not limited to, a solid material, a fibrous material, a macroporous material, a powdered material, or the like, or any combination thereof. The internal surface(s) can comprise that/those of at least one independent support within the reaction chamber. A suitable support can comprise, but is not limited to, a solid material, a mesh material, a fibrous material, a porous material, a powdered material, or beads of a material, or a mixture thereof. The mesh material can comprise, for example, a polymer such as polyolefin, polyester, nylon, cellulose, polystyrene, polycarbonate, polysulfone, or a mixture thereof. The fibrous material can comprise, for example, a polymer such as polyolefin, polyester, nylon, cellulose, polystyrene, polycarbonate, polysulfone, or a mixture thereof. The porous material can comprise, for example, a sintered powder, or a macroporous membrane. The macroporous membrane can comprise, for example, a polymeric material such as polysulfone, polyvinylidene difluoride, nylon, cellulose acetate, polymethacrylate, polyacrylate, or a mixture thereof. The bead material can be selected such that suitable support can be provided for a reagent and/or a reactant ingredient involved in the control reaction and/or the test reaction. Suitable beads can comprise those marketed as DYNABEADS® by Dynal Biotech of Oslo, Norway. The beads can comprise, for example, magnetic beads. The support can have at least one of the following benefits. Firstly, it can increase the surface area where the reagent or other reactant ingredient involved in the control reaction and/or the test reaction, can attach, and/or where the control reaction and/or the test reaction can occur within the chamber. This can decrease the reaction time, and/or the chances for an undesirable process (e.g., contamination, clotting, etc) to occur. Secondly, it can increase the capillary force to the fluid sample by decreasing the capillary distance of the reaction chamber.

The reagent and/or the reactant ingredient involved in the control reaction and/or the test reaction can be coated or otherwise supported on at least one internal surface of the chamber. If the reagent and/or the reactant ingredient are to be supported on the internal chamber walls or the electrodes, the chemicals can be applied by use of printing techniques, e.g., ink jet printing, screen printing, lithography, and the like. In an alternative embodiment, a solution containing the reagent or the reactant ingredient can be applied to an internal surface within the chamber and allowed to dry. The reagent and/or the reactant ingredient can dissolve by a fluid sample or a buffer or other solvent added to the chamber. At least one reagent or the reactant ingredient may not be dissolved by a fluid sample or a buffer or other solvent added to the chamber. At least one reagent or reactant ingredient can be immobilized using, for example, a porous membrane whose porosity is smaller than the particle size of the reagent or the reactant ingredient, or a magnet which can restrain movement of magnetic beads coated with the reagent or the reactant ingredient, or the like. The reagent and/or the reactant ingredient can be coated or otherwise supported uniformly on at least part of one or more internal surfaces. Alternatively, the reagent and/or the reactant ingredient can be coated or otherwise supported at different portions of the chamber (e.g., different portions of the same internal surface of the same chamber, or on different internal surfaces of the same chamber, or different internal surfaces of different chambers).

In some embodiments, a chamber of the biosensor can include two internal surfaces, one or both of which can include an electrically conductive material. The electrically conductive material can be co-extensive with one or both of the internal surfaces. Such an internal surface can serve as an electrode. The electrode can be electrically connected with a meter, or the like, via a contact pad. Description of exemplary biosensors and methods of manufacture can be found, for example, in U.S. Patent Application Publication No. 20060266644, filed May 25, 2005, and U.S. Patent Application Publication No. 20070205103, filed Nov. 21, 2005, both entitled "METHOD AND APPARATUS FOR ELECTROCHEMICAL ANALYSIS", each of which is incorporated herein by reference in its entirety. If the biosensor include two electrically conductive internal surfaces which serve as two different electrodes, the two internal surfaces can be separated from each other by, for example an electrically insulating material. In other embodiments, all the internal surfaces of the biosensor can be electrically insulating.

If the biosensor includes multiple chambers, an internal surface extending across at least two chambers can include an electrically conductive material which is substantially co-extensive with the internal surface, and therefore, be continuously electrically conductive. As used herein, substantially indicates that at least about 20%, or at least about 30%, or at least about 40%, or at least about 50%, or at least about 60%, or at least about 70%, or at least about 80%, or at least about 90%, or at least about 95% of the internal surface is covered by the electrically conductive material. Merely by way of example, a biosensor can include a first chamber and a second chamber in serial fluid connection through a sample passageway. A sample can flow from the chamber to the second chamber upon opening a vent in the second chamber. The two chambers can be defined by a first internal surface, a second internal surface, a spacer layer and an aperture in the spacer layer. The control system and the electrical control signal can be located or generated in the first chamber, and at least part of the testing system and the electrical test signal can be located or generated in the second chamber. The first internal surface can include an electrically conductive material which is substantially co-extensive with the first internal surface and can serve as the working electrode. The second internal surface can include an electrically conductive material which is substantially co-extensive with the second internal surface and can serve as the counter electrode. The working electrode and the counter electrode can be separated by an electrically insulating spacer layer between the first internal surface and the second internal surface. The working electrode and the counter electrode can be electrically connected to a meter via contact pads in order to measure the electrical control signal and the electrical test signal. The control reaction can be activated upon application of the sample to the first chamber to generate the electrical control signal. Upon opening the vent, the sample can flow into the second chamber where the test reaction can be activated by applying an external voltage. The control signal and the test signal can be measured and/or recorded using the same meter, and can be differentiated by the time points when the external voltage is applied.

If the biosensor includes multiple chambers, an internal surface extending across at least two chambers can include an electrically conductive material which is substantially co-extensive with the internal surface, but can include a scratch. Such a scratch can be located at, for example, near the sample passageway between the two chambers. The scratch can generate a break in the electrically conductive material in the chamber. The break can be affected by patterning the conductive film when it is laid down or by creating the break during manufacture. The scratch can be affected by scratching the electrically conductive material, scraping part of the electrically conductive material away, chemically etching the electrically conductive material, laser ablating the conductive electrically conductive material or other methods. A scratch in the electrically conductive material can serve to, in part, define the active electrode area in the chamber by electrically isolating the electrically conductive area in the chamber from that in the other chamber. The scratch can be wide enough to reliably break the electrical conduction of the internal surface where the scratch reside, but not so wide as to prevent fluid from crossing it, such as, for example, under capillary action. The scratch can be from about 1 micrometer to 10 millimeters, or from about 10 micrometers to about 1 millimeter, or from about 20 micrometers to about 200 micrometers. The distance between the scratch and the sample passageway can be less than about 1%, or less than about 5%, or less than about 10%, or less than about 15%, or less than about 20%, or less than about 25%, or less than about 30%, or less than about 35%, or less than about 40%, or less than about 45%, or less than about 50%, or less than 55% of the length of the chamber where the scratch resides.

In some embodiments, the biosensor can include two electrodes, a working electrode and a counter electrode. The two electrodes can be located on different internal surfaces of the biosensor. Merely by way of example, the two electrodes can be opposing to each other. The two electrodes can be opposing to each other and offset by a distance. The two electrodes can be coplanar and separated from each other by a distance. Such an implementation can rely on discharge of the electrochemical potential difference in the sensor or neutralizing electrochemical compounds to shorten duration of the control reaction. The neutralizing electrochemical compound can be coated on an electrode. In other embodiments, the biosensor can include more than two electrodes. Merely by way of example, the biosensor can include a reference electrode, or more than one working electrode.

Embodiments of the application include use of a biosensor as described above. Merely for the purpose of convenience, methods of using a biosensor described herein are described in terms of a biosensor with two chambers in serial fluid communication with a sample passageway. The exemplary biosensor includes a control system and a testing system. The control system includes an electrochemical reaction to generate an electrical control signal. The testing system includes an immunological reaction and an electrochemical detection to generate an electrical test signal. The electrochemical reaction of the control system and the immunological reaction of the test reaction occur in the first chamber, while the electrochemical detection occurs in the second chamber. It is understood that the use of this embodiment is for illustration purpose only, and is not intended to limit the scope of the disclosure.

In use, a user can first introduce a fluid sample into the first chamber. The sample can be drawn into the first chamber under the influence of capillary or wicking action. The sample can be drawn into the first chamber by an external force generated by a device such as, for example, a syringe, and/or a pump, and/or the user. The first chamber can comprise a vent that is open to the atmosphere, thus allowing air displaced by the sample to escape. Alternatively, the filling of first chamber by the fluid sample can displace air to the second chamber. The volume of first chamber can be chosen so as to be at least equal to and preferably larger than the volume of the second chamber.

Entry of a sample, such as whole blood containing a composition of interest (e.g., an antigen) into the first chamber, can activate the control reaction and the immunological reaction.

After a given time, for example, about 10 to about 600 seconds, a vent at the distal end of the second chamber can be opened by, for example, piercing, tearing or punching. This can allow displaced air to escape and transfer of reacted fluid sample by capillary action to the second chamber. The second chamber can comprise at least one reactant ingredient for the electrochemical assessment of the composition of interest. The electrochemical detection can be activated upon application of an external voltage and generate an electrical test signal.

The electrical control signal and the test electrical signal can be measured using the same potentiostat, and the signals can be recorded on the same figure. The electrical control signal and the test electrical signal can be differentiated based on the time point when the external voltage is applied. Viability of the control system or the testing system can be determined by comparing the control signal to a pre-determined standard value.

Embodiments of the present application are further illustrated by the following examples.

EXAMPLE

The following non-limiting examples are provided to further illustrate embodiments of the present application. It should be appreciated by those of skill in the art that the techniques disclosed in the examples that follow represent approaches discovered by the inventors to function well in the practice of the application, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the application.

Example 1

FIG. 1 shows an exploded view of an exemplary electrochemical biosensor with a single chamber. 1 denotes a bottom electrode; 2 denotes an insulating separator or a spacer layer. There is an aperture in the spacer layer along part of its length. 3 denotes a top electrode. Top electrode 3 has a first aperture along part of its length and a second aperture at an angle with the first aperture. The first aperture of top electrode is substantially parallel to the aperture of spacer layer 2. 4 denotes a cover over the fill chamber denoted by 5. 6 denotes a reaction chamber. Fill chamber 5 is defined by bottom electrode 1, cover 4, aperture in top electrode 3 and aperture in spacer layer 2. Reaction chamber 6 is also defined by bottom electrode 1, cover 4, top electrode 3, aperture in top electrode 3 and aperture in spacer layer 2. The control system and the testing system can be located in reaction chamber 6.

Example 2

Figure 2:
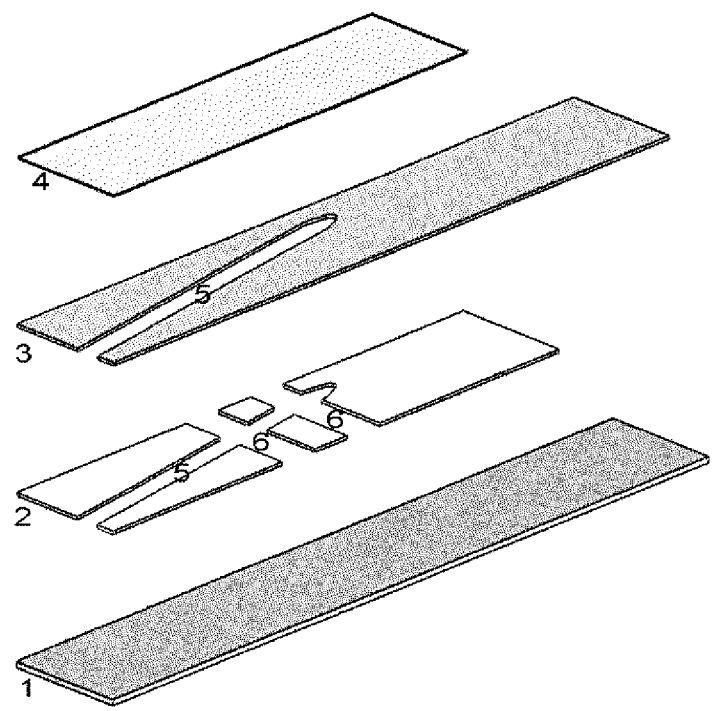
FIG. 2 shows an exploded view of an exemplary electrochemical biosensor with two chambers.

FIG. 2 shows an exploded view of an exemplary electrochemical biosensor with two chambers. 1 denotes a bottom electrode; 2 denotes an insulating separator or a spacer layer. There is an aperture in the spacer layer along part of its length. 3 denotes a top electrode. Top electrode 3 has a first aperture along part of its length, a second aperture at an angle with the first aperture, and a third aperture at an angle with the first aperture and substantially parallel with the second aperture. The first aperture of top electrode is substantially parallel to the aperture of spacer layer 2. 4 denotes a cover over the fill chamber denoted by 5. 6 denotes a reaction chamber. Fill chamber 5 is defined by bottom electrode 1, cover 4, aperture in top electrode 3 and aperture in spacer layer 2. Two reaction chambers 6 are also defined by bottom electrode 1, cover 4, top electrode 3, aperture in top electrode 3 and aperture in spacer layer 2. There is a sample passageway between the two reaction chambers. The control system and the testing system can be located in different reaction chambers 6.

Example 3

Figure 3:
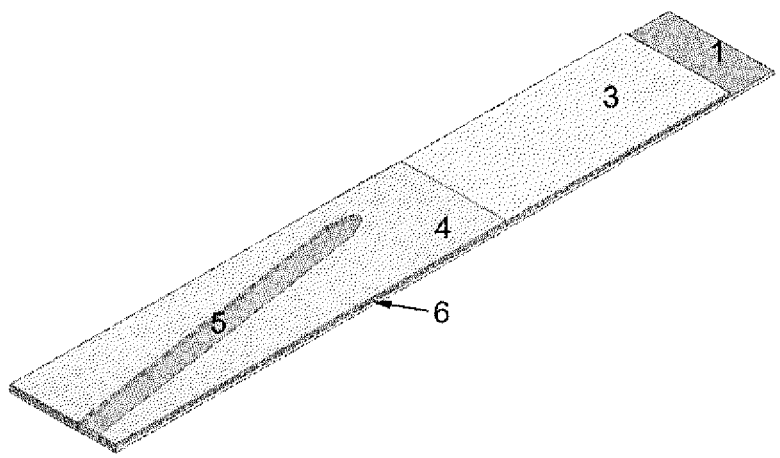
FIG. 3 shows an exemplary electrochemical biosensor.

FIG. 3 shows an exemplary electrochemical biosensor. 1 denotes a bottom electrode; Insulating separator or a spacer layer is not shown in the figure. 3 denotes a top electrode. 4 denotes a cover over the fill chamber denoted by 5. 6 denotes a reaction chamber. The control system and the testing system can be located in reaction chamber 6.

Example 4

Figure 4:
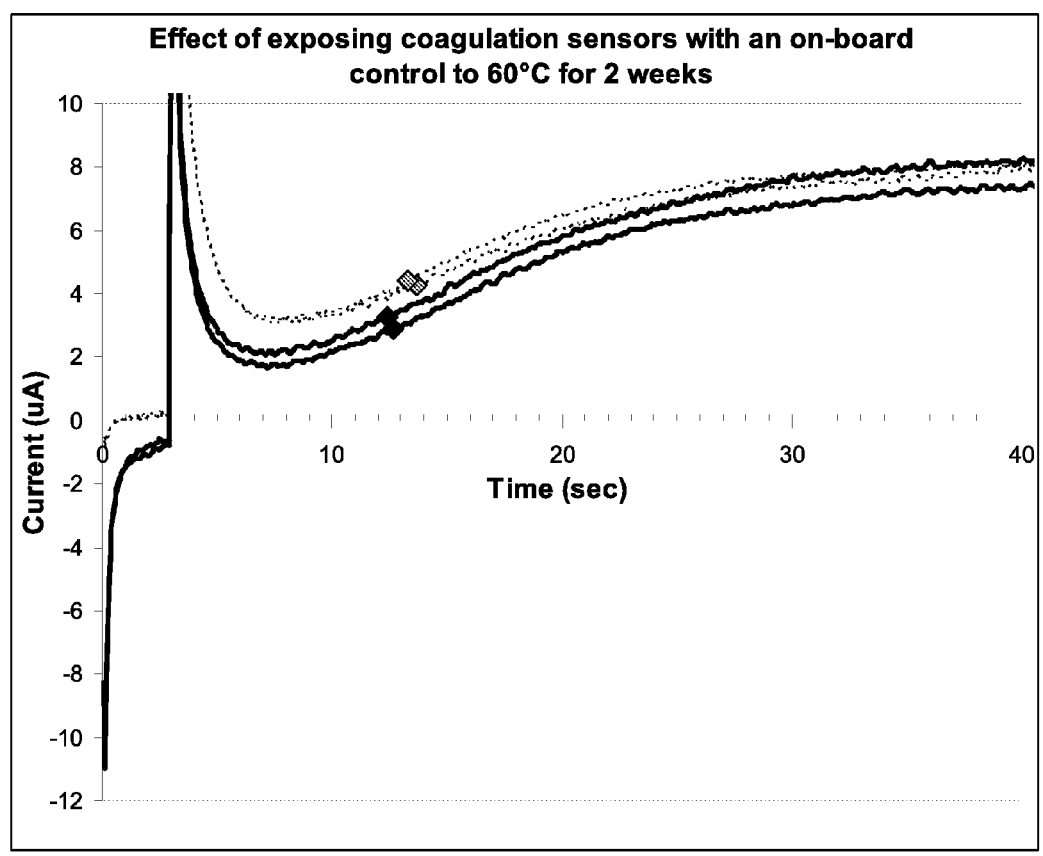
FIG. 4 shows comparison of measurements using coagulation biosensors after different storage conditions.

FIG. 4 shows comparison of measurements using coagulation biosensors after different storage conditions. The current recording started when normal blood was added to the biosensor. For about the first 3 seconds no external voltage was applied to the biosensor. The current generated by the biosensor itself was measured. After about 3 seconds the potentiostat applied about 0.3V across the biosensor and measured the resulting current. The points that are marked with diamonds represent the time at which the sample was deemed to have clotted according to a predetermined algorithm. The thick solid lines represent two biosensors stored at room temperature. The thin dotted lines represent two biosensors stored at about 60° C. for two weeks.

In this example, the on-board control reaction was measured within about the first 3 seconds. The biosensors exposed to high temperature had a much reduced current spike compared to those stored properly at room temperature. The control reaction can be quantified by measuring the area under the curve. The time over which the area under the curve is calculated need not be the full 3 second that the control reaction ran for. In this example, calculating the area over about the first second or about the first 2 seconds can improve the discrimination between acceptable and unacceptable biosensors.

The coagulation test reaction was assessed after about 3 seconds. The biosensors exposed to high temperature show a slight prolongation of their clot time, suggesting mild damage to the reagents in the biosensor.

The various methods and techniques described above provide a number of ways to carry out the application. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some preferred embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform methods in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

In some embodiments, the numbers expressing quantities of ingredients, properties such as molecular weight, reaction conditions, and so forth, used to describe and claim certain embodiments of the application are to be understood as being modified in some instances by the term "about" or "substantially". For example, "about" or "substantially" can indicate ±20% variation of the value it descries, unless otherwise stated. Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

In some embodiments, the terms "a" and "an" and "the" and similar references used in the context of describing a particular embodiment of the application (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. No language in the specification should be construed as indicating any non-claimed element essential to the practice of the application.

Preferred embodiments of this application are described herein, including the best mode known to the inventors for carrying out the application. Variations on those preferred embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

What is claimed is:

1. A sensor for assessing a sample, wherein the sensor comprises an on-board control system and a testing system within a single reaction chamber, wherein the testing system comprises reactant ingredients for performing a test reaction on the sample, wherein the control system comprises at least one control reagent selected from iodine, ascorbate, ferricyanide, ferrocyanide, 4-amino-2-chlorophenol, or a combination thereof, and wherein the at least one control reagent is not an N-oxide compound and is free of nitroso functional groups; and wherein the at least one control reagent mediates a control reaction that generates a control signal, and wherein the control signal indicates viability of the test reaction or at least one of the reactant ingredients involved in the test reaction, and wherein the at least one control reagent is different from the reactant ingredients involved in the test reaction.

2. The sensor of claim 1, wherein the control signal comprises at least one selected from an electrical signal, an optical signal, a color, and a chemical signal.

3. The sensor of claim 1, wherein the control system comprises an electrochemical control system.

4. The sensor of claim 3, wherein the control reaction is assessed without an external voltage.

5. The sensor of claim 3, wherein the control system comprises at least two electrodes, wherein the at least one control reagent is coated on at least one of the electrodes.

6. The sensor of claim 5, wherein the at least two electrodes are coplanar or opposing to each other.

7. The sensor of claim 3, wherein the control reaction generates an electromotive force.

8. The sensor of claim 7, wherein the electromotive force is generated by dissolution of the at least one control reagent into the sample.

9. The sensor of claim 3, wherein the at least one control reagent comprises ferricyanide.

10. The sensor of claim 9, wherein the control system comprises at least two electrodes, wherein the ferricyanide is coated on at least one of the electrodes from about $10 \times 10^{-6}$ to about $200 \times 10^{-6}$ moles per square meter.

11. The sensor of claim 1, wherein the control reaction is activated upon contacting the at least one control reagent with the sample, wherein the contacting initiates the generation of the control signal.

12. The sensor of claim 11, wherein the control signal generated is dependent upon an external stress, wherein the external stress comprises at least one selected from temperature, pH, humidity, oxygen, light, shelf time, prior liquid contact, and a chemical contamination.

13. The sensor of claim 1, wherein the testing system comprises at least one selected from an immunological testing system, a blood glucose testing system, and a blood coagulation testing system.

14. The sensor of claim 1, wherein the control system is located in a first chamber, wherein a part of the testing system is located in a second chamber.

15. The sensor of claim 14, wherein the first chamber and the second chamber are in parallel fluid connection or in serial fluid connection via a sample passageway.

16. A method of determining viability of a test reaction or at least one of the reactant ingredients involved in the test reaction comprising:
applying a sample to the sensor of claim 1,
detecting the control signal,
comparing the control signal with a standard signal to determine viability of the test reaction or at least one of the reactive ingredients involved in the test reaction.

17. The method of claim 16, wherein the control system comprises an electrochemical control system, wherein the control reaction is assessed without an external voltage.

18. The method of claim 17, wherein the at least one control reagent comprises ferricyanide.

19. The method of claim 17, wherein the sample comprises blood, wherein the test reaction measures blood coagulation rate.

20. A sensor for assessing a sample, wherein the sensor comprises an on-board control system and a testing system within a single reaction chamber, wherein the testing system comprises reactant ingredients for performing a test reaction on the sample, wherein the control system comprises at least one control reagent selected from iodine, ascorbate, ferricyanide, ferrocyanide, 4-amino-2-chlorophenol, or a combination thereof, and wherein the at least one control reagent is not an N-oxide compound and is free of nitroso functional groups; and wherein the at least one control reagent mediates a control reaction that generates a control signal, and wherein the control signal indicates viability of the test reaction or at least one of the reactant ingredients involved in the test reaction, and wherein the at least one control reagent is different from the reactant ingredients involved in the test reaction, the sensor further comprising a neutralizing agent, wherein the neutralizing agent neutralizes the control signal via a neutralizing effect.

21. The sensor of claim 20, wherein the neutralizing effect comprises at least one selected from a chemical reaction and a physical effect.

22. The sensor of claim 21, wherein the physical effect comprises at least one selected from precipitation and diffusion.

* * * * *